United States Patent [19]

Seiler, Jr.

[11] 4,111,207
[45] Sep. 5, 1978

[54] NOTCHED TUBULAR CUTTING INSTRUMENT

[75] Inventor: William Seiler, Jr., Van Nuys, Calif.

[73] Assignee: David Kopf Instruments, Tujunga, Calif.

[21] Appl. No.: 736,313

[22] Filed: Oct. 28, 1976

[51] Int. Cl.² .............................................. A61B 17/32
[52] U.S. Cl. .................................... 128/305; 30/241; 128/276
[58] Field of Search ...................... 128/2 B, 305, 276; 30/241

[56] References Cited

U.S. PATENT DOCUMENTS

| | | | |
|---|---|---|---|
| 3,606,878 | 9/1971 | Kellogg, Jr. | 128/305 |
| 3,815,604 | 6/1974 | O'Malley et al. | 128/305 |
| 3,882,872 | 5/1975 | Douvas et al. | 128/305 |
| 4,011,869 | 3/1977 | Seiler, Jr. | 128/305 X |

*Primary Examiner*—Robert W. Michell
*Assistant Examiner*—Michael H. Thaler

[57] ABSTRACT

A notched tubular cutting instrument for use in vitrectomy is provided. An elongated tubular housing is formed with a cutting orifice in its tip. A resilient, inner tubular blade reciprocates within the housing. The housing is bent to bias the blade against the edges of the cutting orifice. The cutting orifice is a notch in the tubular housing having a cutting edge and two side edges. The cutting edge has a rake of more than 10°. The side edges and cutting edge continuously guide the blade across the orifice and provide a shearing action between the blade and the cutting edge.

4 Claims, 4 Drawing Figures

U.S. Patent  Sept. 5, 1978  4,111,207
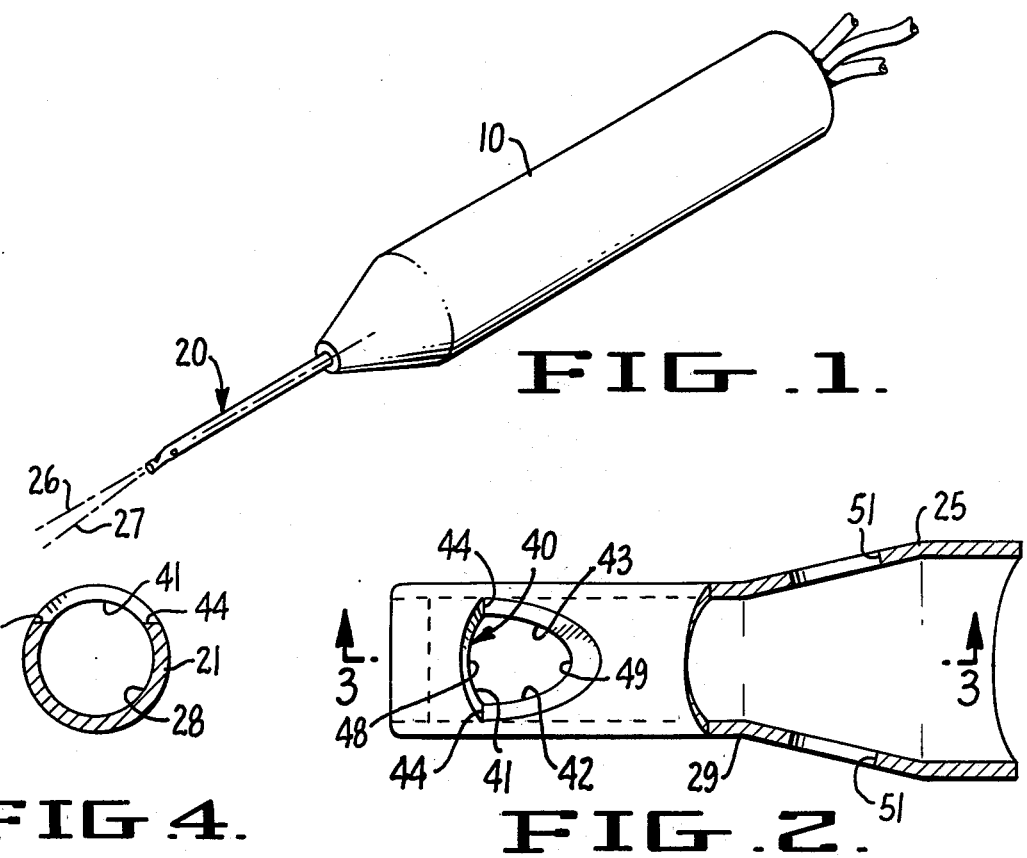
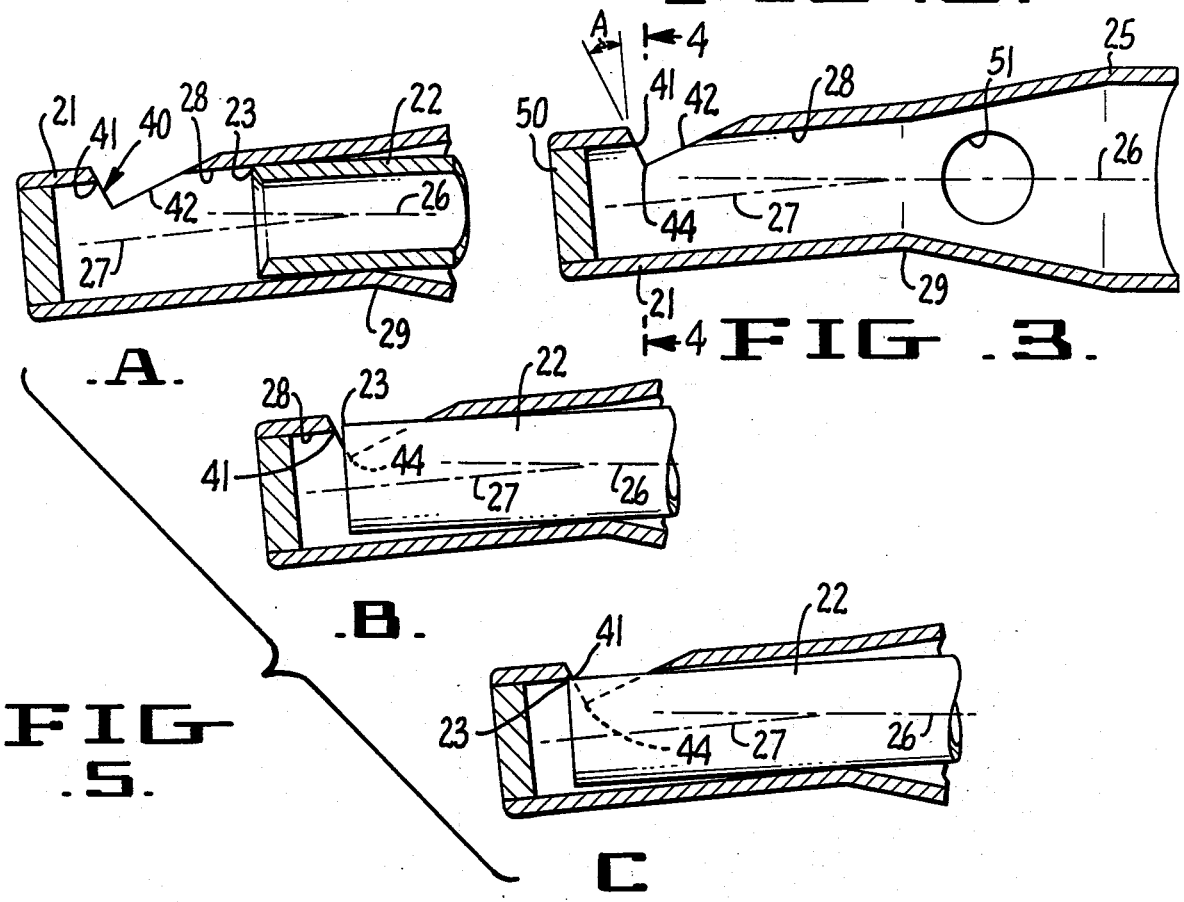

NOTCHED TUBULAR CUTTING INSTRUMENT

This invention relates generally to cutting instruments and more particularly to a cutting instrument useful in vitreous surgery.

This invention is an improvement over the instrument shown in U.S. patent application, Ser. No. 600,897, filed on Aug. 1, 1975, now U.S. Pat. No. 4,011,869 and entitled "Tubular Cutting Instrument". The present invention provides a notched orifice or opening which enables the instrument to be effective on large particles of vitreous matter and fibrous material which "bridges" cutting orifices of the prior art including application Ser. No. 600,897, now U.S. Pat. No. 4,011,869.

The specification of application Ser. No. 600,897, filed Aug. 1, 1975, now U.S. Pat. No. 4,011,869 is incorporated by reference herein. The internal components of body 10 and the characteristics of the tubular members (except for the cutting orifice and the plug in the tip of the housing) are the same for this invention as in Ser. No. 600,897, now U.S. Pat. No. 4,011,869.

The critical feature of this invention is the shape of the cutting orifice. The orifice is notched to facilitate use of the instrument on large pieces of vitreous material and the like. Furthermore, the orifice is formed with edges that guide the blade across the orifice while maintaining virtually zero clearance between the leading edge of the blade and the edges of the orifice. This guiding effect is accomplished by providing the cutting edge of the orifice at a rake angle of greater than 10°.

A primary object of the invention is to provide a cutting instrument utilizing a pair of coaxial elongated tubular members which is capable of cutting relatively large pieces of material relative to the diameter of the tubular members.

A further object of this invention is to provide a cutting instrument useful in vitreous surgery capable of cutting relatively large pieces of vitreous matter and fibrous material which "bridges" cutting orifices of the prior art.

Further objects and advantages of the invention will become apparent from the following description of a preferred embodiment and the drawings, wherein:

FIG. 1 is a perspective view of the invention;

FIG. 2 is a plan view, partially in section, of the tubular housing;

FIG. 3 is a sectional view of the tubular housing along the line 3—3 of FIG. 2;

FIG. 4 is a sectional view of the tubular housing along the line 4—4 of FIG. 3; and FIG. 5 is a schematic representation of the cutting action of the invention.

Referring to FIG. 1, the body 10 of the instrument is held in the surgeon's hand and the cutting tip 20 is inserted into the vitreous cavity for removing vitreous and the like from the eye.

The internal components of body 10 are as described in application Ser. No. 600,897, now U.S. Pat. No. 4,011,869. These components provide the driving mechanism of the instrument.

The present invention is in the cutting tip 20 of the instrument and resides primarily in the shape and characteristics of the cutting orifice 40.

As shown in FIG. 5A, the tip 21 of elongated tubular housing 25 is formed with a notched cutting orifice 40 described in greater detail below. A blade 22 comprising a resilient, inner tubular member is slidably mounted coaxialy within tubular housing 25. The tip 21 of tubular housing 25 is bent about an axis extending vertically out of the drawing from the point identified with reference numeral 29. Housing 25 is bent in a direction such that tip 21 and orifice 40 are displaced in a direction towards the inner tubular member or blade 22. The longitudinal axis of housing 25 is shown as reference numeral 26, and the longitudinal axis of tip 21 is shown as reference numeral 27. This bending of housing 25 causes the blade 22 to be resiliently urged against cutting orifice 40 to ensure clean cutting of the tough and extremely thin vitreous fibers.

The cutting action takes place between the leading edge 23 of blade 22 and the cutting edge 41 of orifice 40. As shown best in FIG. 3, cutting edge 41 lies in a plane forming a rake angle A with a plane perpendicular to the longitudinal axis 27 of tip 21. Rake angle A may range from 10° to 45°. The preferred angle is 20°. Side edges 42 and 43 of orifice 40 lie in a plane perpendicular to the plane of cutting edge 41, as shown best in FIG. 3. The intersection of these planes (i.e., base 44), is formed with a 0.005 inch radius.

Side edges 42 and 43 and cutting edge 41 guide the blade or inner tubular member 22 across orifice 40 as shown best in FIGS. 5A, B and C. As the cutting edge 23 of blade 22 enters the orifice 40, it is resiliently urged against side edges 42 and 43 by reason of the bend in housing 25. As the cutting edge 23 passes the base 44 of notched opening 40, a portion of the leading edge 23 of blade 22 tends to rise above the inner surface 28 of tip 21 as shown in FIG. 5B. By orienting cutting edge 41 at a rake angle A of 10° to 45°, the leading edge 23 of blade 22 is guided downwardly from the position shown in FIG. 5B to the position shown in FIG. 5C and a clean cut is made. Thus, the side edges 42 and 43 and cutting edge 41 continuously guide blade 22 across notched opening 40 and provide a shearing action between blade 22 and cutting edge 41. If the plane of cutting edge 41 were oriented perpendicularly to the longitudinal axis of tip 21, leading edge 23 of blade 22 would jam against cutting edge 41.

Orifice 40 forms a notched opening in housing 21, the lowermost portion of which is base 44. Plug 50 seals the end of tip 21. Base 44 is located axially intermediate the ends 48 and 49 of notched opening 40. Cutting edge 41 and base 44 are located as close to plug 50 as possible, in order to allow cutting as near as possible to an obstruction such as the far wall of the eye. In the embodiment shown, base 44 is located 0.029 inches from the outer surface of plug 50. Plug 50 is 0.010 inches thick.

Base 44 is located radially inward of the inner wall 28 of tip 21. The depth of base 44 from inner wall 28 is less than the inner radius of tip 21 in order to have continuous guiding of blade 22 by side edges 42 and 43 and cutting edge 41. In the preferred embodiment, base 44 of notched orifice 40 is located at a depth one-third of the inner diameter of tip 21. For a housing 21 with an inner diameter of 0.038 inches, base 44 is positioned approximately 0.012 inches downwardly from the inner surface 28 of tip 21.

Infusion ports 51 are provided to replenish vitreous material removed during surgery.

The surfaces which form side edges 42 and 43 and cutting edge 41 are shown as planar surfaces in FIG. 3. These surfaces may be curvilinear.

I claim:

1. In a cutting instrument having an elongated tubular housing having a tip formed with a cutting orifice, a blade comprising a resilient inner tubular member slidably mounted coaxially within said tubular housing, driving means for reciprocating said blade across said cutting orifice, and a bend in said tubular housing displacing said tip and said cutting orifice in a direction toward said blade, the improvement comprising:

said cutting orifice being formed in the tip of said housing as a notched opening defined by a pair of side edges and a cutting edge which come together to form the base of said notched opening, said cutting edge extending from said base distally to one end of said opening, said pair of side edges extending from said base proximally to the opposite end of said opening, said base being located longitudinally intermediate the ends of said opening, said cutting edge having a rake angle greater than 10° and less than 45°, whereby said cutting edge and side edges continuously guide said blade across said notched opening and provide a shearing action between said blade and cutting edge.

2. The cutting instrument of claim 1 wherein said housing is a tubular member with an outer wall and an inner wall, wherein said base is located between the outer wall of said housing and the longitudinal center line of said housing at a depth which exceeds the wall thickness of said housing.

3. The instrument of claim 2 wherein said cutting edge lies in a plane.

4. The instrument of claim 3 wherein said side edges lie in a plane which forms a right angle with the plane of said cutting edge.

* * * * *